United States Patent [19]
Hirano et al.

[11] Patent Number: 5,891,920
[45] Date of Patent: Apr. 6, 1999

[54] MEDICINAL ADJUVANTS CONSISTING OF N-SUBSITITUTED-O-TOLUIDINE DERIVATIVES, AND PERCUTANEOUSLY ABSORBABLE PREPARATIONS COMPRISING THE ADJUVANTS

[75] Inventors: Munehiko Hirano; Mitsuru Kuribayashi; Mitsuhiko Kido, all of Tsukuba, Japan

[73] Assignee: Hisamitsu Pharmaceutical Co., Inc., Tosu, Japan

[21] Appl. No.: 809,812

[22] PCT Filed: Oct. 4, 1995

[86] PCT No.: PCT/JP95/02033

§ 371 Date: Mar. 31, 1997

§ 102(e) Date: Mar. 31, 1997

[87] PCT Pub. No.: WO96/11022

PCT Pub. Date: Apr. 18, 1996

[30] Foreign Application Priority Data

Oct. 5, 1994 [JP] Japan ..................................... 6-268292
Jul. 12, 1995 [JP] Japan ..................................... 7-197938

[51] Int. Cl.$^6$ ..................... A61K 31/165; A61K 47/16
[52] U.S. Cl. ............................. 514/625; 514/625
[58] Field of Search ..................... 514/629, 625

[56] References Cited

U.S. PATENT DOCUMENTS 4,752,612  6/1988  Saito et al. ............................. 514/420
5,162,315  11/1992 Rajadhyaksha et al. ............... 514/211

FOREIGN PATENT DOCUMENTS 0 127 468 A2  12/1984  European Pat. Off. .
5173115       6/1976   Japan .

OTHER PUBLICATIONS

Database WPI Week 8748, Derwent Publications Ltd., AN 87–337226, XP 002046755 Japanese Publication No. 62–240628A, Publication Date: Oct. 21, 1987.

*Primary Examiner*—Phyllis G. Spivack
*Attorney, Agent, or Firm*—Kubovcik & Kubovcik

[57] ABSTRACT

A drug solubilizer or drug-absorption accelerator of Formula I is disclosed wherein $R_1$ and $R_2$ are herein defined

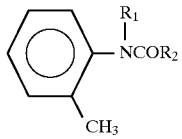

10 Claims, 5 Drawing Sheets

MEDICINAL ADJUVANTS CONSISTING OF N-SUBSITITUTED-O-TOLUIDINE DERIVATIVES, AND PERCUTANEOUSLY ABSORBABLE PREPARATIONS COMPRISING THE ADJUVANTS

TECHNICAL FIELD

This invention relates to a drug solubilizer and a drug-absorption accelerator which are for use in administration by percutaneous absorption of the drug in a preparation for external use, and also to a percutaneously absorbable preparation. More particularly it relates to (1) a drug solubilizer which consists of an N-substituted-o-toluidine derivative and is excellent in drug solubility, safety, stability, compatibility with a base and feeling at the time of use, (2) a drug-absorption accelerator which contains said toluidine derivative as an absorption acceleration effective ingredient, increases the drug in permeability and transmittability through the skin and is low in irritation to the biomembranes and (3) a percutaneously absorbable preparation containing said solubilizer and said absorption accelerator.

BACKGROUND ART

There have conventionally been developed ointments, poultices, tape-aids, lotions, suppositories, eye lotions and the like in the field of preparations for external use. Among these preparations, percutaneously absorbable preparations have recently attracted public attention and are arousing an increasing interest in themselves. The reasons for this are that in cases where a drug, the pharmacological action of which is expected, is administered locally or systemically so as to be percutaneously absorbed, it is advantageously possible to keep the efficacy of the drug, adjust the rate of absorption thereof easily thereby enabling the prevention of medicinal side effects caused by overdosing the drug, lessen the influence of metabolism exerted by the effect of the drug caused by the initial passage thereof through the liver as is experienced in case of oral administration, thereby enabling the drug to be effectively utilized, and administer comparatively safe even such a drug as to cause liver troubles and the like. In addition to the above preparations, there has now been developed a form of preparation, called "TTS", having a high function to control the release thereof.

(1) In these externally usable preparations attempted to be percutaneously absorbed, it is important to release a drug from a base which contains it, that is, it is necessary for the drug to be efficiently transferred from the base to the skin. To this end, generally importance is placed in the state of dissolution of the drug in the base at the stage of designing these preparations. In other words, how the drug exists in the base will have remarkable effects on not only its physico-chemical stability but also its release from the base, percutaneous absorption efficiency and consequent medicinal efficacy. Thus, it comes to be very important when designing preparations, to select a solubilizer which is excellent in solubilization of the drug and exerts an effect on uniform dispersion of the drug into the base.

Solubilizers now used for drugs include fatty acids such as oleic acid and myristic acid, fatty acid esters such as isopropyl myristate and isopropyl palmitate, essence oils such as limonene, peppermint oil and eucalyptus oil, polyhydric alcohols such as polyethylene glycol and propylene glycol, surface-active agents, glycol salicylate and crotamiton, among which crotamiton is frequently used as a solubilizer for difficultly soluble drugs. For example, crotamiton is used as a solubilizer for indomethacin in Japanese Patent Gazette No. Hei 3-3368 (or No. 3368/91), as a solubilizer for steroids in Japanese Pat. Appln. Laid-Open Gazette No. Sho 51-73115 (No. 73115/76) and as a precipitation preventer for valeric acid dexamethasone in Japanese Patent Gazette No. Hei 2-36572. In addition, Japanese Pat. Appln. Laid-Open Gazette No. Sho 59-116212 discloses an indomethacin-containing creamy preparation comprising crotamiton as a solubilizer for the drug.

These solubilizers, however, raise problems as to precipitation of a drug in the crystal form because of shortage of their solubilizability (capability of solubilization), limitation of their use because of their odor, their bleeding with time due to their poor compatibility with the base, and their instability such as their decomposition or discoloration with the lapse of time. Further, these solubilizers cause undesirable side reactions and the like due to their irritation to the skin and they thus exhibit no fully satisfactory results in not a few cases.

(2) On the other hand, absorbability and permeability of the drug are taken as important factors when percutaneously absorbable preparations are designed. This is because the healthy skin is naturally protective against stimuli provided from the outside and, therefore, it makes the absorption and permeation of a drug therethrough comparatively difficult. Accordingly, even if the drug is administered in the form of a percutaneously absorbable preparation, it is difficult at the present to let the drug be absorbed easily through the skin in such an amount as is necessary for fully realizing an intended medicinal efficacy.

Further, in cases where the drugs are administered to let them be absorbed not through the skin but through other biomembranes such as the mouth, rectum, palate, nose or hypoglottis, there are found many drugs which are difficultly permeable or penetrable through the biomembrane concerned depending on the kind of the drugs or which are low in bioavailability.

Thus, there are sought drug-absorption accelerators which fully enhance drugs in permeability, penetrability and absorbability through the skin and other biomembranes, enable the drugs to exhibit their full pharmacological effects in their practical service concentration and are low in local and systemic toxicities and high in usability and safety.

When a drug is attempted to be percutaneously absorbed at the present, there is used an absorption accelerator which enables the drug to be absorbed in a sufficient amount by weakening the barrier function of the stratum corneum where the absorption is to be effected. Of known absorption accelerators, those such as salicylic acid, urea, dimethylsulfoxide and dimethylacetoamide are known for their dissolution of corneum, and, however, the use of them will not necessarily exhibit satisfactory percutaneous absorption of drugs. Propylene glycol, glycerin, pyrrolidone sodium carbonate and the like can keep the corneum humid, but it is hardly appreciated that they are effective in percutaneous absorption of drugs. Further, as absorption accelerators there are known fatty acid esters such as isopropyl myristate and isopropyl adipate, surfactants such as sodium laurylate and polyoxyethylene-sorbitan monolaurate, thioglycerol, urea derivatives or mixtures of a pyrrolidone-based compound and halogenated hydrocarbons (Japanese Pat. Appln. Laid-Open Gazette No. Sho 60-13720), calcium thioglycolate (Japanese Pat. Appln. Laid-Open Gazette No. Sho 60-11431), 1-substituted azacycloalkane-2-one (Japanese Pat. Appln. Laid-Open Gazette No. Sho 60-37092), crotonyl-N-ethyl-o-toluidine (Japanese Pat. Appln. Laid-Open Gazette No. Hei 2-258720) and the like.

Conventional known drug-absorption accelerators, however, are not yet powerful enough to enhance the bioavailability of drugs which are low in permeability and penetrability into the biomembranes, and, thus, they do not provide a practical pharmacological effect in not a few cases. In addition, there are some of conventional absorption accelerators, which themselves exhibit skin irritation and sensitization and present textural discoloration and severe serious side effects due to their successive administration. Furthermore, they are reported to corrode synthetic resins because of their property as a powerful solvent, thereby to elute irritative substances, sensitizers and the like from drug containers, clothing, haberdashery and the like. Under such circumstances, the known absorption accelerators still now leave problems as to practicality such as limitations on general application of the accelerators and method of use thereof.

In view of the above problem (1) as to conventional techniques, a first object of this invention is to provide drug solubilizers having the following excellent characteristics. The solubilizers so provided are such that they make drugs difficult to precipitate with time because of their excellent capability of solubilizing drugs, are physicochemically stable without their decomposition, phase separation and unpleasant odor in the base, are an inactive substance without interaction with the drug and are high in safety because of few side reactions such as skin sensitization.

A second object of this invention is to provide drug-absorption accelerators which can solve the problems (2) as to the conventional techniques. The accelerators so provided are such that they enable drugs to be remarkably enhanced in permeability or penetrability through the skin, are highly safe because of their weak skin irritation and no sensitization and are excellently compatible with the base without giving any change in compatibility between the drug and the base.

Moreover, a third object of this invention is to provide percutaneously absorbable preparations comprising various kinds of drugs and the drug solubilizer of this invention or the drug-absorption accelerator of this invention.

DISCLOSURE OF THE INVENTION

The present inventors made intensive studies in an attempt to solve the above problems and, as the result of their studies, they have found that an N-substituted-o-toluidine derivative represented by the following formula (I) is excellent in solubilizing a wide range of drugs, is effective even for drugs which have exhibited their unsatisfactory solubility, dispersibility and transferability to the affected part of a patient when the known solubilizer was used and is also physicochemically stable with excellent feeling given when in use. This invention is based on the above finding.

At the same time, it has been found that the drug-absorption accelerator which contains the N-substituted-o-toluidine derivative as a drug-absorption accelerating active component, exhibits a more excellent drug-absorption accelerating action than conventionally known ones and is, furthermore, lower in irritability to the skin. This invention is also based on this finding.

The crux of this invention resides in a drug solubilizer consisting of at least one compound selected from N-substituted-o-toluidine derivatives, in a drug-absorption accelerator containing said at least one compound as a drug-absorption accelerating active component and in a percutaneously absorbable preparation comprising said drug solubilizer and said drug-absorption accelerator, the N-substituted-o-toluidine derivatives being represented by the following formula (I)

wherein $R_1$ is a lower alkyl group having 1–4 carbon atoms and $R_2$ is an alkyl group having 1–8 carbon atoms.

The N-substituted-o-toluidine derivatives, which are the drug solubilizers or drug-absorption accelerators of this invention, are compounds having an amide skeleton. The derivatives themselves have already been known, and an example wherein the derivative is used as one component of a hair-growing preparation is disclosed in Japanese Patent Application Laid-Open Gazette No. Hei 2-11509 (No. 11509/90). However, there has not been found any example wherein the derivative is used as a drug solubilizer or drug-absorption accelerator of a preparation for external use intended for percutaneous absorption of the drug therefrom. Thus, it was not known until the finding by the present inventors that the N-substituted-o-toluidine derivatives exhibited excellent performances as a drug solubilizer or drug-absorption accelerator in percutaneously absorbable preparations.

The content of the N-substituted-o-toluidine derivative in the percutaneously absorbable preparation of this invention is 0.01 to 20% by weight, desirably 0.1 to 20% by weight, more desirably 0.1 to 10% by weight, most desirably 0.5 to 5% by weight based on the total weight of the preparation. The use of the derivative in an amount of less than 0.01% by weight will fail in attaining a sufficient effect as the drug solubilizer or drug-absorption accelerator, while the use thereof in an amount exceeding 20% by weight will make it difficult to give stable preparations.

The drugs to be used in the percutaneously absorbable preparation of this invention are not particularly limited but may arbitrarily be selected from known drugs.

First, the drugs to be used in a case where the N-substituted-o-toluidine derivative is used as the drug solubilizer include antipyretic-antiinflammatory agents, steroidal antiinflammatory agents, vasodilators, antiarrhythmic agents, hypotensive agents, antitussive-expectorants, local anesthetics, hormone preparations, drugs for asthma and nasal allergy, antihistamines, anticoagulants, cerebral vasodilators, drugs for metabolic diseases, vitamin preparations, antifungal agents, hypolipidemic drugs, therapeutic agents for urination disorder, hypoglycemic agents, hypnotics and antibiotics.

The antipyretic-antiinflammatory agents include sulindac, tolmetin, oxaprozin, pranoprofen, tiaprofen, suprofen, oxaprozin, etodolac, tenidap, bermoprofen, mofezolac, actarit, ampiroxicam, zaltoprofen, indometacin, salicylic acid, aspirin, acetaminophen, diclofenac, ibuprofen, felbinac, ketorolac, roxoprofen, naproxen, ketoprofen, flufenamic acid, ibufenac, fenbufen, alclofenac, phenylbutazone, mefenamic acid, bendazac, piroxicam, flurbiprofen and pentazocine tartrate. The steroidal antiinflammatory agents include hydrocortisone, prednisolone, fluocinolone acetonide, fludroxycortide, methylprednisolone, hydrocortisone acetate, clobetasone butyrate, dexamethasone, betamethasone acetate, diflucortolone valerate, clobetasol propionate and fluocinonide.

The vasodilators include diltiazem, verapamil, pentaerythritol tetranitrate, dipyridamole, isosorbide dinitrate, nifedipine and nitroglycerin. The antihypertensive-antiarrhythmic agents include propranolol, atenolol, pindolol, quinidine sulfate, ajmalin, alprenolol hydrochloride, metoprolol tartrate, nadolol, timolol maleate and disopyramide. The hypotensive agents include clonidine hydrochloride, captopril, prazosin hydrochloride, penbutolol sulfate, guanabenz acetate and arotinolol hydrochloride. The antitussive-expectorants include procaterol hydrochloride, terbutaline sulfate, fenoterol hydrobromide, tulobuterol hydrochloride and formoterol fumarate. The local anesthetics include benzocaine, procaine, lidocaine and tetracaine. The hormone preparations include estrogen, estradiol, estriol, testosterone, norethisterone, progesterone, prostaglandin and insulin. The drugs for asthma and nasal allergy include ketotifen fumarate, azelastine hydrochloride and cromoglicic acid sodium. The antihistamines include cyproheptadine hydrochloride, diphenhydramine hydrochloride, fenbenzamin and mequitazine. The anticoagulants include heparin. The cerebral vasodilators and the drugs for metabolic diseases include vinpocetine, flunarizine hydrochloride, nicaravan, fasudil hydrochloride, vinconate hydrochloride, nicardipine hydrochloride, ifenprodil tartrate and isoxsuprine hydrochloride. The vitamin preparations include alfacalcidol and ergocalciferol. The antifungal agents include fluconazole, neticonazole hydrochloride, terbinafine hydrochloride, ketoconazole, miconazole nitrate and econazole nitrate. The hypolipidemic drugs include pravastatin, lovastatin, fluvastatine and simvastatine. The therapeutic agents for urination disorder include amsulosin hydrochloride, terazosin hydrochloride, naphthopidil, urapidil and bunazosin hydrochloride. The hypoglycemic agents include glibenclamide and gliclazide. The hypnotics include phenobarbital and amobarbital. The antibiotics include tetracycline and chloramphenicol.

Although examples of the drug have been given above, the drug is not limited to them. Further, these drugs can also be used in the form of medically acceptable inorganic or organic salts.

Then, a description will now be made of the drug to be used in the percutaneously absorbable preparation of this invention wherein the N-substituted-o-toluidine derivative is used as the drug-absorption accelerator.

The drugs include steroidal antiinflammatory agents such as prednisolone, dexamethasone, hydrocortisone, fluocinolone acetonide, betamethasone valerate, betamethasone dipropionate, clobetasone butyrate and prednisolone succinate; nonsteroidal antiinflammatory agents such as indometacin, diclofenac, ibuprofen, ketoprofen, flufenamic acid, ketorolac, flurbiprofen, felbinac, suprofen, pranoprofen, tiaprofen, roxoprofen, tenidap and nimesulide, and esters thereof; antiallergic agents such as tranilast, azelastine, ketotifen, ibudilast, oxatomide, emedastine and ebastine; antihistamines such as diphenhydramine, chlorpheniramine, promethazine and tripelennamine; central nervous system acting drugs such as chlorpromazine, nitrazepam, diazepam, phenobarbital and reserpine; hormones such as insulin, testosterone, norethisterone, norethisterone acetate, methyltestosterone, progesterone and estradiol; antihypertensive agents such as clonidine, reserpine and guanethidine sulfate; cardiotonics such as digitoxin and digoxin; antiarrhythmic agents such as propranolol hydrochloride, procainamide hydrochloride, ajmalin, pidolol and tulobuterol hydrochloride; coronary vasodilators such as nitroglycerin, isosorbide dinitrate, papaverine hydrochloride and nifedipine; local anesthetics such as lidocaine, benzocaine, procaine hydrochloride and tetracaine; analgesics such as morphine, aspirin, codeine, acetanilide and aminopyrine; skeletal muscle relaxants such as eperisone, tizanidine, tolperisone, inaperisone and pridinol mesylate; antifungal agents such as acetophenylamine, nitrofurazone, pentamycin, naphthiomate, miconazole, omoconazole, clotrimazole, butenafine hydrochloride and bifonazole; antineoplastic agents such as 5-fluorouracil, busulfan, actinomycin, bleomycin and mitomycin; therapeutic agents for urination disorder such as terodiline hydrochloride, oxybutynin hydrochloride, prazosin hydrochloride, amsulosin hydrochloride, bunazosin hydrochloride, naphthopidil, urapidil, vamicamide, terazosin hydrochloride and oxybutynin; antiepileptics such as nitrazepam and meprobamate; antiparkinson agents such as chlorzoxazone and levodopa; assistants for quitting smoking such as nicotine; vitamins; and prostaglandin. Of course, the drugs are not limited to those described above. Further, these drugs can also be used in the form of medically acceptable organic or inorganic salts.

The amount of drug used is preferably 0.001 to 20% by weight, more preferably 0.5 to 10% by weight, of the total amount of the percutaneously absorbable preparation, though it is not particularly limited.

The dosage form of the percutaneously absorbable preparation of this invention is not particularly limited, but may be any one selected from among conventional poultice, tape-aid, ointment, gel, cream, gel-like cream, lotion, spray, reserver-having patch, liniment, aerosol and so forth.

The poultice and tape-aid among the percutaneously absorbable preparations of this invention will now be described below.

In preparing the poultice, a hydrophilic base comprising a water-soluble polymer, a polyhydric alcohol and water is used as a base in consideration of long-term stability, releasability and percutaneous absorbability of a drug and safety for the skin.

The water-soluble polymer to be used in the hydrophilic base may be one or more members suitably selected from the group consisting of gelatin, casein, pullulan, dextran, sodium alginate, soluble starch, carboxystarch, dextrin, carboxymethylcellulose, sodium carboxymethylcellulose, methylcellulose, ethyl-cellulose, hydroxyethylcellulose, polyvinyl alcohol, polyethylene oxide, polyacrylic acid, polyacrylamide, polysodium acrylate, polyvinylpyrrolidone, carboxy-vinyl polymer, polyvinyl ether, methoxyethylene-maleic anhydride copolymer, N-vinylacetamide, copolymer comprising N-vinylacetamide and acrylic acid and/or acrylate salt and so forth. The amount of the water-soluble polymer used is 1 to 30% by weight, preferably 1 to 20% by weight, more preferably 1 to 15% by weight, based on the total weight of the preparation. When the amount is less than 1% by weight, the resulting preparation will have too low a viscosity to retain its shape, while when it exceeds 30% by weight, the resulting mixture of the constituents will have a high viscosity to lower the workability in preparing a homogeneous dispersion of the constituents or in applying the dispersion.

The polyhydric alcohol is one or more members suitably selected from the group consisting of polyethylene glycol, propylene glycol, dipropylene glycol, polypropylene glycol, 1,3-butylene glycol, 1,4-butylene glycol, isobutylene glycol, glycerol, diglycerol, sorbitol and so forth. The amount of the polyhydric alcohol used is 10 to 90% by weight, preferably 10 to 70% by weight, more preferably 20 to 60% by weight. When the amount is less than 10% by weight, the resulting preparation will exhibit poor humectant effect, while when it exceeds 90% by weight, the solubility of the water-soluble polymer will be adversely affected. The amount of water used is 10 to 90% by weight, preferably 20 to 80% by weight. The water serves to solubilize the water-soluble polymer to thereby make the polymer develop its thickening, cohesive and shape-retaining properties.

If necessary, the base of the poultice may further contain one or more crosslinking agents in addition to the above essential components. The crosslinking agents include polyvalent metal compounds such as aluminum hydroxide, aluminum chloride, calcium hydroxide, calcium chloride, aluminum sulfate, aluminum ammonium sulfate, aluminum potassium sulfate, magnesium aluminometasilicate and dihydroxyaluminum aminoacetate; and compounds each having at least two epoxy groups in the molecule such as ethylene glycol diglycidyl ether, polyethylene glycol diglycidyl ether, propylene glycol diglycidyl ether, polypropylene glycol diglycidyl ether, polytetramethylene glycol diglycidyl ether, glycerol polyglycidyl ether, polyglycerol polyglycidyl ether, sorbitol polyglycidyl ether, sorbitan polyglycidyl ether, pentaerythritol polyglycidyl ether, resorcinol diglycidyl ether, neopentyl glycol diglycidyl ether and 1,6-hexanediol diglycidyl ether.

Further, the poultice may contain one or more other components suitably selected from among fillers such as kaolin, zinc oxide, titanium dioxide, talc, bentonite and synthetic aluminum silicate; antiseptics such as thymol, methyl paraben and ethyl paraben; antioxidants such as ascorbic acid, stearic esters, dibutylhydroxytoluene, butylhydroxyanisole, gallic esters, vitamin E, vitamin E acetate and disodium edetate; ultraviolet absorbers such as 2-hydroxy-4-methoxybenzophenone, ethyl p-aminobenzoate, 2-(2-hydroxy-5-methylphenyl) benzotriazole, glycol salicylate, methyl salicylate and phenyl salicylate; and emulsifying agents such as fatty acid esters of sorbitan, fatty acid esters of glycerol, fatty acid esters of decaglycerol, fatty acid esters of polyoxyethylene sorbitan, fatty acid esters of polyethylene glycol and polyoxyethylene alkyl ethers.

It is essential that the support of the poultice be made of a material which has no influence on the release of a drug, i.e., that the support neither interacts with a drug nor adsorbs a drug. The support is selected from the group consisting of films and sheets of polyethylene, polypropylene, polyvinyl chloride, polyester, nylon and polyurethane; laminates each comprising one or more members selected from the group consisting of these films and sheets and one or more members selected from the group consisting of porous materials, expanded materials and woven and nonwoven fabrics of these polymers. The release sheet of the poultice according to this invention may be selected from the group consisting of films of polyethylene, polypropylene and polyester; products of release treatment of these films with silicone compounds; release paper and so forth.

The preparation of the poultice will now be described, though the poultice can be easily prepared by known processes.

For example, a drug is solubilized in the N-substituted-o-toluidine derivative to form a solution (A) which may, if necessary, be incorporated with one or more additives selected from the group consisting of a stabilizer, an antioxidant, an ultraviolet absorber, an emulsifying agent, an antiseptic, an antimicrobial and so forth. Separately, a water-soluble polymer is mixed into, dispersed and solubilized in a polyhydric alcohol and water to form a homogeneous paste (B). The solution (A) is added to the paste (B) to form a homogeneous dispersion. This dispersion is spread directly on a support or alternatively it is once spread on a paper or film treated with a releasing agent and thereafter transferred from the paper or film to a support by pressing. Thus, a poultice according to this invention is prepared. The above-mentioned order of procedures for mixing the base materials, drug and other components is just one example, and is not limited to said order of procedures.

Then, the tape-aid of this invention will now be described. The adhesive base to be used in making the tape-aid may be suitably selected from known ones in consideration of safety for the skin, drug-releasing properties, adhesion to the skin and so on. Preferable adhesive bases include acrylic adhesives, rubber-based adhesives and silicone-based adhesives.

Particularly preferable acrylic adhesives include homopolymers and copolymers of alkyl (meth)acrylates wherein the alkyl has 4 to 18 carbon atoms and copolymers of such alkyl (meth)acrylates with other functional monomers.

The alkyl (meth)acrylates include butyl acrylate, isobutyl acrylate, hexyl acrylate, octyl acrylate, 2-ethylhexyl acrylate, isooctyl acrylate, decyl acrylate, isodecyl acrylate, lauryl acrylate, stearyl acrylate, methyl methacrylate, ethyl methacrylate, butyl methacrylate, isobutyl methacrylate, 2-ethylhexyl methacrylate, isooctyl methacrylate, decyl methacrylate, isodecyl methacrylate, lauryl methacrylate and stearyl methacrylate.

The above functional monomers include hydroxyl group-bearing monomers, carboxyl group-bearing monomers, amido group-bearing monomers, amino group-bearing monomers and pyrrolidone ring-bearing monomers. The hydroxyl group-bearing monomers include hydroxyalkyl (meth)acrylates such as 2-hydroxyethyl (meth)acrylate and hydroxypropyl (meth)acrylate. The carboxyl group-bearing monomers include α,β-unsaturated carboxylic acids such as acrylic acid and methacrylic acid; monoalkyl maleates such as butyl maleate; maleic acid; fumaric acid; and crotonic acid. Further, maleic anhydride as well as maleic acid can also be used as a comonomer. The amido group-bearing monomers include alkyl(meth)acrylamides such as acrylamide, dimethylacrylamide and diethylacrylamide; N-alkoxymethyl(meth)acrylamides such as N-butoxymethylacrylamide and N-ethoxymethylacrylamide; and diacetone acrylamide. The amino group-bearing monomers include dimethylaminoethyl acrylate. The pyrrolidone ring-bearing monomers include N-vinyl-2-pyrrolidone.

The rubber-based adhesives include natural rubber, synthetic isoprene rubber, polyisobutylene, polyvinyl ether, polyurethane, polyisoprene, polybutadiene, styrene-butadiene copolymers, styrene-isoprene copolymers and styrene-isoprene-styrene block copolymers.

The silicone-based adhesives include those mainly comprising polyorganosiloxane or polydimethylsiloxane.

The tackifiers to be used in the tape-aids include rosin and hydrogenated, disproportionated, polymerized or esterified derivatives thereof; terpene resins such as α-pinene and β-pinene; terpene-phenol resins; aliphatic, aromatic, alicyclic or copolymer-type petroleum resin; alkylphenyl resin and xylene resins.

The softeners used in the tape-aid plasticizes and softens the base polymer to permit the tape-aid to keep adhesion to the skin properly. The softeners include polybutene; polyisobutylene; liquid paraffin; higher fatty acid esters such as isopropyl myristate; silicone oils; and vegetable oils such as almond oil, olive oil, camellia oil, persic oil and peanut oil.

The supports to be used in the tape-aids are preferably ones which do not exert any influence on the release of drugs. The supports may be stretchable or non-stretchable ones. The supports are selected from synthetic resin membranes which are films and sheets of polyethylene, polypropylene, polybutadiene, ethylene-vinyl acetate copolymers, polyvinyl chloride, polyester, nylon and polyurethane; or selected from laminates, porous membranes, foamed bodies, paper, textiles and nonwoven fabrics of said synthetic resins.

The tape-aid according to this invention can be easily prepared by known processes. For example, a tape-aid based on a synthetic rubber can be prepared by mixing an adhesive base with a softening agent and a tackifier under heating at 120° to 160° C. by the use of a mixing machine such as a kneader or mixer, adding a drug and a N-substituted-o-toluidine derivative to the obtained mixture, and applying the resulting mixture to a support either by spreading the mixture directly on a film of polypropylene or polyester or by spreading the mixture on a paper or film treated with a releasing agent and thereafter transferring the spread mixture on the paper or film to a desired support by pressing.

The base polymer of the synthetic rubber-based tape-aid may be selected from conventional ones in consideration of safety for the skin, releasability of a drug and adhesion to the skin. From the standpoint of the release characteristics of, for example, a nonsteroidal anti-inflammatory agent, however, it is preferable that the base polymer be a styrene-isoprene-styrene block copolymer having a particularly low polarity. Such block copolymers include Cariflex TR-1107, TR-1111, TR-1112 and TR-1117 (trade names, products of Shell Chemical Co., Ltd.) and Solprene 428 (trade name, a product of Phillips Petroleum Co., Ltd.). These styrene-isoprene-styrene block copolymers may be each used together with other polymer such as polyisobutylene. Vistanex (trade name, a product of Exxon Chemical Co., Ltd.) is preferably used as the polyisobutylene.

The softening agent used in the above tape-aid serves to plasticize or soften the styrene-isoprene-styrene block copolymer used as the base polymer to allow the tape-aid to keep proper adhesion to the skin. The softening agent may be selected from the group consisting of almond oil, olive oil, camellia oil, persic oil, peanut oil, liquid paraffin and so forth. The amount of the softening agent used is preferably 150 to 350 parts by weight per 100 parts by weight of the styrene-isoprene-styrene block copolymer.

The content of a drug in the above tape-aid is preferably 70 to 1200 $\mu$g per cm$^2$ of the tape-aid from the standpoints of therapeutically effective release of a drug and availability thereof, though it is not particularly limited. Preferable proportions of a drug, tackifier, N-substituted-o-toluidine derivative, styrene-isoprene-styrene block copolymer and softening agent are as follows.

That is, the tape-aid comprises 0.5 to 10% by weight of a drug, 5 to 70% by weight of a rosin ester derivative, 0.1 to 20% by weight of the N-substituted-o-toluidine derivative, 5 to 40% by weight of a styrene-isoprene-styrene block copolymer and 10 to 75% by weight of a softening agent, each percentage being based on the total amount.

The acrylic tape-aid can be made by dissolving or dispersing an adhesive base, a drug, an absorption accelerator and, if necessary, various adjuvants in a proper solvent, applying the thus obtained solution or dispersion directly to a support and drying the resulting layer to form an application layer having a thickness of 30 to 200 $\mu$m. Alternatively, the tape-aid can be made also by applying the solution or dispersion to a release paper for protection, drying the resulting layer and making the thus formed application layer adhere to a support. The solvent to be used in the above process is not particularly limited but may be any organic solvent which is compatible with all of the constituents such as adhesive base and drug. The solvent includes aromatic hydrocarbons such as toluene, benzene and xylene; and halogenated hydrocarbons such as carbon tetrachloride, chloroform and methylene chloride.

Now, brief description will be made of other percutaneously absorbable preparations such as ointment, gel, cream, gel-type cream, lotion, reserver-having patch, liniment and aerosol according to this invention.

The ointment according to this invention comprises at least higher fatty acid such as myristic acid or an ester thereof, a wax such as spermaceti, a surfactant such as polyoxyethylene and a hydrocarbon such as hydrophilic vaseline in addition to a drug and N-substituted-o-toluidine derivative.

The ointment can be prepared by, for example, mixing 5 to 15% by weight of a higher fatty acid or an ester thereof with 1 to 10% by Weight of a surfactant, 0.5 to 10% by weight of a drug and 0.5 to 10% by weight of the N-substituted-o-toluidine derivative either at room temperature or under heating, adding 4 to 10% by weight of a wax and 50 to 90% by weight of a hydrocarbon to the obtained mixture, heating or heat-melting the resulting mixture, keeping the mixture at 50° to 100° C. to make the whole mixture a transparent solution, homogenating the solution with a homomixer, and lowering the temperature of the resulting solution to room temperature under stirring.

The gel according to this invention comprises at least a lower alcohol such as ethanol, water, a gelling agent such as a carboxyvinyl polymer and a neutralizing agent such as triethanolamine in addition to a drug and N-substituted-o-toluidine derivative.

The gel can be prepared, for example, as follows: 0.5 to 5% by weight of a gelling agent is swollen with at most 55% by weight of water; separately, 0.5 to 10% by weight of a drug is solubilized in 0.5 to 10% by weight of N-substituted-o-toluidine derivative and the obtained solution is further solubilized in a mixture comprising at most 40% by weight of a glycol and at most 60% by weight of a lower alcohol; the obtained solution is mixed with the gelling agent swollen above; and the resulting mixture is adjusted to pH4–7 by the addition of a neutralizing agent, thus forming a gel according to this invention.

The cream according to this invention comprises at least a higher fatty acid ester such as myristate, water, a hydrocarbon such as liquid paraffin and an emulsifying agent such as polyoxyethylene alkyl ether in addition to a drug and N-substituted-o-toluidine derivative.

The cream can be prepared by stirring a mixture comprising a drug, the N-substituted-o-toluidine derivative, a higher fatty acid ester, water, a hydrocarbon and an emulsifying agent in proper amounts.

A gel-like cream has intermediate properties between a gel and a cream and can be prepared by adding a gelling agent such as a carboxyvinyl polymer to components of cream as described above and adjusting the resulting mixture to pH4–8, preferably pH5–6.5 by the addition of a neutralizing agent such as diisopropanolamine.

The gel-like cream according to this invention can be prepared, for example, as follows: 0.5 to 10% by weight of a drug is solubilized in 0.5 to 10% by weight of the N-substituted-o-toluidine derivative and the obtained solution is further solubilized in a mixture comprising at most 25% by weight of a higher fatty acid ester and at most 40% by weight of a lower alcohol, followed by the addition of at most 5% by weight of an emulsifying agent; separately, 0.5 to 5% by weight of a gelling agent is swollen with water; the swollen agent is mixed with the solution prepared above;

and the obtained mixture is homogenized with a homomixer and adjusted to pH4–8 by the addition of a neutralizing agent.

The lotion according to this invention comprises at least a lower alcohol such as ethanol and water and/or a glycol in addition to a drug and N-substituted-o-toluidine derivative.

The lotion can be prepared by stirring a mixture comprising a drug, the N-substituted-o-toluidine derivative, a lower alcohol and water and/or a glycol in proper amounts.

The reserver-having patch according to this invention comprises at least (1) a backing layer, (2) a drug reserving layer, (3) a drug releasing layer and (4) a pressure-sensitive adhesive layer, wherein the drug reserving layer (2) is a base comprising one mixture selected from the group consisting of (a) mixture comprising at least a glycol, a lower alcohol, water and a water-soluble polymer, (b) a mixture comprising at least an aliphatic alcohol and a polyhydric alcohol and (c) a mixture comprising at least a paraffin and a silicon compound, in addition to a drug and the N-substituted-o-toluidine derivative.

The liniment according to this invention comprises at least an alcohol such as ethanol or polyethylene glycol, water and an ester of fatty acid such as adipic acid or sebacic acid in addition to a drug and the N-substituted-o-toluidine derivative.

The liniment can be prepared by dissolving 0.5 to 10% by weight of a drug in 0.5 to 10% by weight of the N-substituted-o-toluidine derivative and mixing the obtained solution with 10 to 70% by weight of an alcohol, at most 55% by weight of water and at most 60% by weight of a fatty acid ester under stirring.

The aerosol according to this invention comprises at least a lower alcohol, water and dimethyl ether and/or liquefied petroleum gas in addition to a drug and N-substituted-o-toluidine derivative, and may further contain an auxiliary drug such as camphor α-tocopherol or menthol as needed. The aerosol can be prepared by dissolving 0.5 to 10% by weight of a drug in 0.5 to 10% by weight of the N-substituted-o-toluidine derivative, adding a lower alcohol and water to the obtained solution, charging the obtained mixture into an aerosol container and press-injecting dimethyl ether and/or liquefied petroleum gas as a propellant into the container.

The percutaneously absorbable preparations according to this invention may further contain various pharmacologically acceptable additives such as a stabilizer, an antioxidant, a perfume, a filler, an ultraviolet absorber, an antihistamine, an antiseptic, an antimicrobial agent and an absorbefacient.

The drug solubilizer of this invention consisting of at least one of the N-substituted-o-toluidine derivatives exhibits excellent solvency for a wide range of drugs and is so excellent in heat stability as to decompose little even under heating at high temperature or to generate little unpleasant odor.

A percutaneously absorbable preparation comprising the solubilizer and a drug, particularly a sticking-type one, is excellent in stability as the preparation and exhibits excellent drug-releasing properties for a long period, so that the drug can be absorbed into the circulatory system through the skin in amounts enough to exhibit the objective effects.

Although the detailed mechanism of action of how the solubilizer exhibits high solvency for a drug and how the preparation containing it is stabilized has not been elucidated, it is believed that the interaction between the highly polar amide skeleton and fat-soluble alkyl groups of the solubilizer enhances the solvency for a drug and prevents a drug from precipitating in the crystal form. Meanwhile, no skin sensitization due to the solubilizer has been observed.

On the other hand, the drug-absorption accelerator of this invention comprising at least one of the N-substituted-o-toluidine derivatives enhances the permeation or transmission of a drug through the skin remarkably, when added to the drug in a proper amount.

When a percutaneously absorbable preparation containing the absorption accelerator is applied to the skin, the drug contained in the preparation can be absorbed easily through the skin. Although the detailed mechanism of action how this effect is exhibited has not been elucidated, it is believed that the absorption accelerator acts on the cell membranes of dermal cells to lower the barrier properties thereof.

When a tape-aid or patch is made by the use of the drug-absorption accelerator, the absorption accelerator does not exert any adverse effect on the properties of the adhesive constituting the tape-aid or patch, so that the tape-aid or the patch can keep its adhesiveness.

BEST MODE FOR CARRYING OUT THE INVENTION

This invention will be further described by the following Examples, Comparative Examples and Test Examples.

| Example 1 lotion | (wt. %) |
|---|---|
| ethanol | 57.0 |
| purified water | 34.0 |
| propylene glycol | 5.0 |
| N-butanoyl-N-ethyl-o-toluidine | 3.0 |
| ketoprofen | 1.0 |

The above components were mixed together under agitation thereby to prepare a lotion comprising ketoprofen.

| Example 2 cream | (wt. %) |
|---|---|
| liquid paraffin | 10.0 |
| medium chain triacylglycerol | 5.0 |
| polyethylene glycol monostearate | 3.0 |
| carboxyvinyl polymer | 1.0 |
| diisopropanolamine | 0.4 |
| methyl p-oxybenzoate | 0.2 |
| indomethacin | 1.0 |
| N-butanoyl-N-ethyl-o-toluidine | 5.0 |
| purified water | balance |

The above components were mixed together under agitation thereby to prepare a cream comprising indomethacin.

| Example 3 ointment | (wt. %) |
| --- | --- |
| white vaseline | 76.0 |
| glycerol monostearate | 10.0 |
| beef tallow | 10.0 |
| silicone oil | 1.0 |
| N-butanoyl-N-ethyl-o-toluidine | 2.0 |
| flurbiprofen | 1.0 |

The above components were mixed together under agitation thereby to prepare an ointment comprising flurbiprofen.

| Example 4 poultice | (wt. %) |
| --- | --- |
| N-butanoyl-N-ethyl-o-toluidine | 1.0 |
| diclofenac | 0.5 |
| purified water | 48.5 |
| gelatin | 8.0 |
| kaolin | 1.0 |
| glycerol | 35.0 |
| polysodium acrylate | 2.0 |
| polyvinyl alcohol | 3.0 |
| aluminum hydroxide | 1.0 |

The above ingredients were solubilized together and agitated thereby to obtain a homogeneous paste. The paste was applied on a polypropylene nonwoven fabric with a spreader to obtain a percutaneously absorbable preparation layer having a thickness of 1 mm. Then, the preparation layer was covered with a polypropylene film and cut into pieces each having a predetermined size thereby to obtain intended pharmaceutical products.

| Example 5 poultice | (wt. %) |
| --- | --- |
| N-butanoyl-N-ethyl-o-toluidine | 2.0 |
| loxoprofen | 1.0 |
| thymol | 0.1 |
| purified water | 62.4 |
| gelatin | 3.0 |
| titanium oxide | 1.0 |
| glycerol | 25.0 |
| polysodium acrylate | 3.0 |
| carboxymethyl cellulose | 1.0 |
| ethylene glycol diglycidyl ether | 1.0 |
| sorbitan fatty acid ester | 0.5 |

The above ingredients were solubilized together and agitated thereby to obtain a homogeneous paste. The paste was applied on a polyester nonwoven fabric with a spreader to obtain a percutaneously absorbable preparation layer having a thickness of 0.5 mm. Then, the preparation layer was covered with a polyethylene film and cut into pieces each having a predetermined size thereby to obtain intended pharmaceutical products.

| Example 6 poultice | (wt. %) |
| --- | --- |
| N-butanoyl-N-ethyl-o-toluidine | 3.0 |
| ibuprofen | 0.5 |
| ethyl paraben | 0.2 |
| purified water | 42.3 |
| methoxyethylene anhydrous maleic acid copolymer | 5.0 |
| synthetic aluminium silicate | 3.0 |
| glycerol | 40.0 |
| polyacrylic acid | 2.0 |

| Example 6 poultice | (wt. %) |
| --- | --- |
| polyvinyl alcohol | 2.5 |
| calcium hydroxide | 1.5 |

The above ingredients were solubilized together and agitated thereby to obtain a homogeneous paste. The paste was applied on a polyurethane film with a spreader to obtain a percutaneously absorbable preparation layer having a thickness of 1 mm. Then, the preparation layer was covered with a polyester film and cut into pieces each having a predetermined size thereby to obtain intended pharmaceutical products.

| Example 7 poultice | (wt. %) |
| --- | --- |
| N-butanoyl-N-ethyl-o-toluidine | 2.0 |
| ketoprofen | 0.5 |
| purified water | 36.0 |
| N-vinylacetamide | 5.0 |
| glycerol | 50.0 |
| polyacrylic acid | 3.0 |
| carboxymethyl cellulose | 1.0 |
| magnesium metasilicate aluminate | 1.5 |
| fatty acid esters of glycerol | 1.0 |

The above ingredients were solubilized together and agitated thereby to obtain a homogeneous paste. The paste was applied on a polyester nonwoven fabric with a spreader to obtain a percutaneously absorbable preparation layer having a thickness of 1 mm. Then, the preparation layer was covered with a polyester film and cut into pieces each having a predetermined size thereby to obtain intended pharmaceutical products.

| Example 8 tape-aid | (wt. %) |
| --- | --- |
| styrene-isoprene-styrene block copolymer | 22.5 |
| polyisobutylene | 5.0 |
| rosin ester | 15.0 |
| liquid paraffin | 56.0 |
| N-butanoyl-N-ethyl-o-toluidine | 1.0 |
| ketotifen | 0.5 |

The above components were agitated under heating, thereby obtaining a paste. The paste was spread on a support to obtain a tape-aid containing ketotifen.

| Example 9 tape-aid | (wt. %) |
| --- | --- |
| styrene-isoprene-styrene block copolymer | 25.0 |
| liquid paraffin | 59.0 |
| alicyclic saturated hydrocarbon resin | 5.0 |
| N-butanoyl-N-ethyl-o-toluidine | 10.0 |
| diclofenac | 1.0 |

The above components were mixed by a kneader to obtain a paste. Thereafter, the paste was applied directly on a PBT woven fabric and then covered with a liner to obtain a tape-aid containing diclofenac.

| Example 10 tape-aid | (wt. %) |
|---|---|
| styrene-isoprene-styrene block copolymer | 20.0 |
| liquid paraffin | 43.5 |
| polyisobutylene | 10.0 |
| rosin ester | 21.5 |
| N-butanoyl-N-ethyl-o-toluidine | 4.0 |
| diclofenac | 1.0 |

The above components were mixed by a mixer to obtain a paste. The paste was applied on a plastic film previously endowed with releasability and then covered with a PET woven fabric and pressure-contact transferred to obtain a tape-aid containing diclofenac.

| Example 11 tape-aid | (wt. %) |
|---|---|
| styrene-isoprene-styrene block copolymer | 15.0 |
| liquid paraffin | 23.0 |
| polyisobutylene | 7.0 |
| rosin ester | 40.0 |
| N-butanoyl-N-ethyl-o-toluidine | 10.0 |
| ketoprofen | 5.0 |

The components of the above prescription were mixed together by a kneader to obtain a paste. The paste was applied on a plastic film previously endowed with releasability, thereon covered with a polypropylene nonwoven fabric and pressure-contact transferred to obtain a tape-aid.

| Example 12 tape-aid | (wt. %) |
|---|---|
| styrene-isoprene-styrene block copolymer | 21.0 |
| liquid paraffin | 66.8 |
| rosin ester | 7.2 |
| N-butanoyl-N-ethyl-o-toluidine | 4.0 |
| flurbiprofen | 1.0 |

A tape-aid containing flurbiprofen was obtained in the same manner as in Example 10.

| Example 13 tape-aid | (wt. %) |
|---|---|
| styrene-isoprene-styrene block copolymer | 21.0 |
| liquid paraffin | 50.0 |
| rosin ester | 20.5 |
| N-butanoyl-N-ethyl-o-toluidine | 5.5 |
| loxoprofen | 3.0 |

The components of the above prescription were mixed together by a kneader to obtain a paste. The paste was applied on a plastic film previously endowed with releasability, thereon covered with a polypropylene woven fabric and pressure-contact transferred to obtain a tape-aid containing loxoprofen.

| Example 14 tape-aid | (wt. %) |
|---|---|
| styrene-isoprene-styrene block copolymer | 22.0 |
| polyisobutylene | 8.0 |
| liquid paraffin | 46.0 |
| rosin ester | 14.0 |
| N-butanoyl-N-ethyl-o-toluidine | 8.0 |
| ketorolac | 2.0 |

The components of the above prescription were mixed together by a kneader to obtain a paste. The paste was applied on a plastic film previously endowed with releasability and, covered thereon with a PBT nonwoven fabric and pressure-contact transferred to obtain a tape-aid.

| Example 15 tape-aid | (wt. %) |
|---|---|
| styrene-isoprene-styrene block copolymer | 15.0 |
| polyisobutylene | 14.0 |
| liquid paraffin | 38.0 |
| rosin ester | 26.0 |
| N-butanoyl-N-ethyl-o-toluidine | 5.0 |
| felbinac | 2.0 |

The components of the above prescription were mixed together by a kneader to obtain a paste. The paste was applied on a plastic film previously endowed with releasability, thereon covered with a polypropylene woven fabric and pressure-contact transferred to obtain a tape-aid.

| Example 16 tape-aid | (wt. %) |
|---|---|
| styrene-isoprene-styrene block copolymer | 27.0 |
| liquid paraffin | 55.0 |
| rosin ester | 7.0 |
| N-butanoyl-N-ethyl-o-toluidine | 10.0 |
| estradiol | 1.0 |

The components of the above prescription were mixed together by a kneader to obtain a paste. The paste was applied on a plastic film previously endowed with releasability and, covered thereon with a PET film and pressure-contact transferred to obtain a tape-aid.

| Example 17 tape-aid | (wt. %) |
|---|---|
| styrene-isoprene-styrene block copolymer | 27.0 |
| liquid paraffin | 55.0 |
| rosin ester | 7.0 |
| N-butanoyl-N-ethyl-o-toluidine | 10.0 |
| isosorbide dinitrate | 1.0 |

A tape-aid containing isosorbide dinitrate was obtained in the same manner as in Example 10.

| Example 18 tape-aid | (wt. %) |
|---|---|
| pressure-sensitive adhesive of acrylic resin solubilizer type (trade name: NISSETSU PE-300) (solid) | 77.0 |
| N-butanoyl-N-ethyl-o-toluidine | 15.0 |
| isosorbide dinitrate | 8.0 |

The above components were mixed together to obtain a paste. The paste was spread on a support and then freed of the solvent by evaporation thereby to obtain a tape-aid containing isosorbide dinitrate.

| Example 19 tape-aid | (wt. %) |
|---|---|
| silicone adhesive (trade name: BIO-PSA X7-2920) (solid) | 89.0 |
| N-butanoyl-N-ethyl-o-toluidine | 7.0 |
| clonidine | 4.0 |

The above components were mixed together to obtain a paste. The paste was spread on a support and then freed of the solvent by evaporation thereby to obtain a tape-aid containing clonidine.

| Example 20 tape-aid | (wt. %) |
|---|---|
| styrene-isoprene-styrene block copolymer | 28.0 |
| liquid paraffin | 30.0 |
| rosin ester | 37.0 |
| N-butanoyl-N-ethyl-o-toluidine | 4.0 |
| estradiol | 1.0 |

A tape-aid containing estradiol was obtained in the same manner as in Example 16.

| Example 21 tape-aid | (wt. %) |
|---|---|
| styrene-isoprene-styrene block copolymer | 15.0 |
| polyisobutylene | 14.0 |
| liquid paraffin | 38.0 |
| rosin ester | 27.0 |
| N-propanoyl-N-ethyl-o-toluidine | 5.0 |
| estradiol | 1.0 |

A tape-aid containing estradiol was obtained in the same manner as in Example 16.

| Example 22 tape-aid | (wt. %) |
|---|---|
| styrene-isoprene-styrene block copolymer | 15.0 |
| polyisobutylene | 14.0 |
| liquid paraffin | 38.0 |
| rosin ester | 27.0 |
| N-butanoyl-N-ethyl-o-toluidine | 5.0 |
| estradiol | 1.0 |

A tape-aid containing estradiol was obtained in the same manner as in Example 10.

| Example 23 tape-aid | (wt. %) |
|---|---|
| styrene-isoprene-styrene block copolymer | 28.0 |
| liquid paraffin | 30.0 |
| rosin ester | 37.0 |
| N-propanoyl-N-ethyl-o-toluidine | 4.0 |
| estradiol | 1.0 |

A tape-aid containing estradiol was obtained in the same manner as in Example 10.

| Example 24 tape-aid | (wt. %) |
|---|---|
| styrene-isoprene-styrene block copolymer | 28.0 |
| liquid paraffin | 30.0 |
| rosin ester | 37.0 |
| N-acetyl-N-ethyl-o-toluidine | 4.0 |
| estradiol | 1.0 |

A tape-aid containing estradiol was obtained in the same manner as in Example 10.

| Example 25 tape-aid | (wt. %) |
|---|---|
| styrene-isoprene-styrene block copolymer | 28.0 |
| liquid paraffin | 30.0 |
| rosin ester | 37.0 |
| N-acetyl-N-ethyl-o-toluidine | 4.0 |
| testosterone | 1.0 |

A tape-aid containing testosterone was obtained in the same manner as in Example 16.

| Example 26 tape-aid | (wt. %) |
|---|---|
| styrene-isoprene-styrene block copolymer | 28.0 |
| liquid paraffin | 30.0 |
| rosin ester | 37.0 |
| N-propanol-N-ethyl-o-toluidine | 4.0 |
| testosterone | 1.0 |

A tape-aid containing testosterone was obtained in the same manner as in Example 16.

| Example 27 tape-aid | (wt. %) |
|---|---|
| styrene-isoprene-styrene block copolymer | 28.0 |
| liquid paraffin | 30.0 |
| rosin ester | 37.0 |
| N-butanoyl-N-ethyl-o-toluidine | 4.0 |
| testosterone | 1.0 |

A tape-aid containing testosterone was obtained in the same manner as in Example 16.

| Comparative Example 1 tape-aid | (wt. %) |
|---|---|
| styrene-isoprene-styrene block copolymer | 28.0 |
| liquid paraffin | 32.0 |
| rosin ester | 39.0 |
| estradiol | 1.0 |

A tape-aid containing estradiol was obtained in the same manner as in Example 10.

| Comparative Example 2 tape-aid | (wt. %) |
|---|---|
| styrene-isoprene-styrene block copolymer | 28.0 |
| liquid paraffin | 30.0 |
| rosin ester | 37.0 |

-continued

| Comparative Example 2 tape-aid | (wt. %) |
|---|---|
| crotamiton | 4.0 |
| estradiol | 1.0 |

A tape-aid containing estradiol was obtained in the same manner as in Example 10.

| Comparative Example 3 tape-aid | (wt. %) |
|---|---|
| styrene-isoprene-styrene block copolymer | 28.0 |
| liquid paraffin | 30.0 |
| rosin ester | 37.0 |
| propylene glycol | 4.0 |
| estradiol | 1.0 |

A tape-aid containing estradiol was obtained in the same manner as in Example 10.

| Comparative Example 4 tape-aid | (wt. %) |
|---|---|
| styrene-isoprene-styrene block copolymer | 28.0 |
| liquid paraffin | 32.0 |
| rosin ester | 39.0 |
| testosterone | 1.0 |

A tape-aid containing testosterone was obtained in the same manner as in Example 16.

| Comparative Example 5 tape-aid | (wt. %) |
|---|---|
| styrene-isoprene-styrene block copolymer | 28.0 |
| liquid paraffin | 30.0 |
| rosin ester | 37.0 |
| dimethyl sulfoxide | 4.0 |
| testosterone | 1.0 |

A tape-aid containing testosterone was obtained in the same manner as in Example 16.

| Comparative Example 6 tape-aid | (wt. %) |
|---|---|
| styrene-isoprene-styrene block copolymer | 28.0 |
| liquid paraffin | 30.0 |
| rosin ester | 37.0 |
| crotamiton | 4.0 |
| testosterone | 1.0 |

A tape-aid containing testosterone was obtained in the same manner as in Example 16.

Test Example 1
Drug dissolution test
(Experimental method)
1. Samples were prepared under various conditions (i.e, at various solubilizer/drug ratios). Each sample was heated at 120° C. to dissolve the drug gradually. The heating was discontinued in at most 2 hours considering the stability of drugs and so on (the compound in which the drug was not dissolved after 2-hour heating was regarded as having no solvency).
2. After the dissolution, the resulting samples were allowed to stand at room temperature for two weeks or longer and observed for whether the drugs were precipitated in the crystal forms or not. The samples not causing apparently recognizable precipitation were further allowed to stand at 5° C.

The results of the tests on dissolution of ketoprofen, indomethacin, isosorbide dinitrate and estradiol are given in Table 1 (comparison among the solubilities of ketoprofen in various solubilizers), Table 2 (comparison among the solubilities of indomethacin in various solubilizers), Table 3 (comparison among the solubilities of isosorbide dinitrate in various solubilizers) and Table 4 (comparison among the solubilities of estradiol in various solubilizers). In these Tables, "acetamiton" (invention solubilizer) refers to N-acetyl-N-ethyl-o-toluidine, and "butamiton" (invention solubilizer) N-butanoyl-N-ethyl-o-toluidine.

TABLE 1

| Drug:Solubilizer | acetamiton | butamiton | EtOH | PEG(400) | PG | IPM |
|---|---|---|---|---|---|---|
| 1:2.5 | ○ | ○ | ○ | ○ | ○ | * |
| 1:1.3 | ○ | ○ | ○ | Δ | Δ | |
| 1:1.0 | ○ | ○ | ○ | * | Δ | |
| 1:0.8 | ○ | ○ | ○ | | Δ | |
| 1:0.7 | ○ | ○ | ○ | | Δ | |
| 1:0.5 | ○ | ○ | ○ | | * | |
| 1:0.4 | ○ | ○ | * | | | |
| 1:0.3 | ○ | Δ | | | | |
| 1:0.2 | Δ | * | | | | |

Note:
* → Deposition before 1 week
Δ → Deposition between 1 to 2 weeks
○ → No Deposition after 2 weeks

TABLE 2

| Drug:Solubilizer | acetamiton | butamiton | EtOH | PEG(400) | PG | IPM |
|---|---|---|---|---|---|---|
| 1:33.0 | ○ | ○ | ○ | ○ | ○ | * |
| 1:10.0 | ○ | ○ | * | ○ | Δ | |
| 1:7.0 | ○ | ○ | | ○ | * | |
| 1:5.0 | ○ | ○ | | ○ | | |
| 1:3.3 | ○ | ○ | | Δ | | |
| 1:2.5 | ○ | ○ | | Δ | | |
| 1:1.3 | ○ | Δ | | * | | |
| 1:1.0 | * | * | | | | |

Note:
* → Deposition before 1 week
Δ → Deposition between 1 to 2 weeks
○ → No Deposition after 2 weeks

TABLE 3

| Drug:Solubilizer | acetamiton | butamiton | EtOH | PEG(400) | PG | IPM |
|---|---|---|---|---|---|---|
| 1:33.0 | ○ | ○ | ○ | ○ | ○ | ○ |
| 1:10.0 | ○ | ○ | ○ | ○ | Δ | * |
| 1:7.0 | ○ | ○ | ○ | ○ | * | |
| 1:5.0 | ○ | ○ | * | ○ | | |
| 1:3.3 | ○ | ○ | | Δ | | |
| 1:2.5 | ○ | ○ | | * | | |
| 1:1.3 | ○ | Δ | | | | |
| 1:1.0 | Δ | Δ | | | | |
| 1:0.8 | * | * | | | | |

Note:
* → Deposition before 1 week
Δ → Deposition between 1 to 2 weeks
○ → No Deposition after 2 weeks

TABLE 4

| Drug:Solubilizer | acetamiton | butamiton | EtOH | PEG(400) | PG | IPM |
|---|---|---|---|---|---|---|
| 1:33.0 | ○ | ○ | ○ | ○ | ○ | ○ |
| 1:10.0 | ○ | ○ | * | Δ | * | * |
| 1:7.0 | ○ | ○ | | * | | |
| 1:5.0 | ○ | ○ | | | | |
| 1:3.3 | ○ | ○ | | | | |
| 1:2.5 | ○ | Δ | | | | |
| 1:1.3 | * | * | | | | |

Note:
* → Deposition before 1 week
Δ → Deposition between 1 to 2 weeks
○ → No Deposition after 2 weeks It can be understood from the results given in Tables 1 to 4 that the N-substituted-o-toluidine derivatives are superior to representative solubilizers now used conventionally in solvency power for drugs and exhibit excellent solvency action for a wide range of drugs.

Test Example 2
Heat stability test
(Experimental method)
1. Stopped sample tubes each containing 100 mg of a solubilizer therein were prepared and heated on a hot plate at 180° C. for 5 hours.
2. The resulting sample solubilizers were observed for state. Further, the sample solubilizers were subjected to GC analysis both before and after the heating to determine the rates of solubilizers remaining after the heating.

In the Table, "acetamiton" refers to N-acetyl-N-ethyl-o-toluidine, and "butamiton" N-butanoyl-N-ethyl-o-toluidine.

TABLE 5

| | acetamiton | butamiton | crotamiton |
|---|---|---|---|
| State of solubilizer | pale-yellow transparent | pale-yellow transparent | dark brown |
| rate of solubilizer remaining | 99.0% | 98.5% | 81.5% |

Note:
Crotamiton generates a strong unpleasant odor after heating.

As apparent from the results given in Table 5, the N-substituted-o-toluidine derivatives of this invention are superior to crotamiton in heat stability.

Test Example 3
Test of preparation for stability
The tape-aids of Examples 20, 23 and 24 and Comparative Examples 1 to 3 were stored at 5° C. for seven weeks, while they were observed with the lapse of time to find whether the drug crystallized or not. The results are given in Table 6.

TABLE 6

| Sample | initial | 1 week | 2 weeks | 3 weeks | 4 weeks | 7 weeks |
|---|---|---|---|---|---|---|
| Ex. 20 | ○ | ○ | ○ | ○ | ○ | ○ |
| Ex. 23 | ○ | ○ | ○ | ○ | ○ | ○ |
| Ex. 24 | ○ | ○ | ○ | ○ | ○ | ○ |
| Comp. Ex. 1 | * | | | | | |
| Comp. Ex. 2 | ○ | ○ | * | | | |
| Comp. Ex. 3 | ○ | * | | | | |

○: no crystallization was found
*: crystallization was found

As apparent from the results in Table 6, the tape-aids of Examples 20, 23 and 24 each containing the N-substituted-o-toluidine derivative contained estradiol in its solubilized state in the base even after the lapse of seven weeks, while the tape-aid of Comparative Example 1 containing no solubilizer, that of Comparative Example 2 containing crotamiton and that of Comparative Example 3 containing propylene glycol suffered from the crystallization of estradiol in their respective bases. Thus, the above results supported the usefulness of N-substituted-o-toluidine derivatives as the solubilizers for estradiol.

Figure 1:
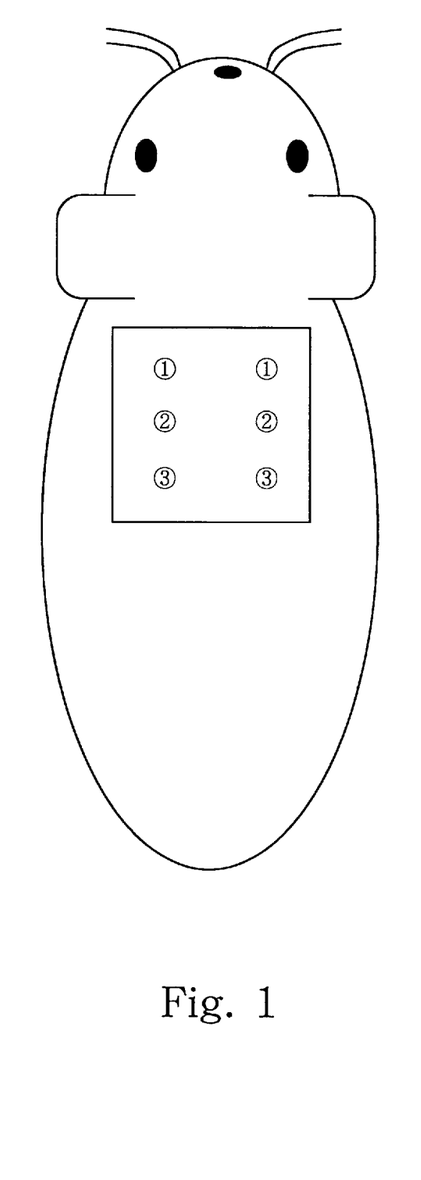
FIG. 1: A view showing the intradermal sensitization test in the neck and back of guinea-pig

Test Example 4
Skin sensitization test
N-substituted-o-toluidine derivatives of this invention were subjected to the skin sensitization test according to the maximization method wherein crotamiton was used as a comparative solubilizer.
<Test compounds and control>
  (1) crotamiton
  (2) N-acetyl-N-ethyl-o-toluidine (hereinafter referred to as "acetamiton")
  (3) N-butanoyl-N-ethyl-o-toluidine (hereinafter referred to as "butamiton")
  (4) 2,4-dinitrochlorobenzene (DNCB; known skin sensitizer)
<Test animal>
  Hartley female guinea pigs (weight: 320 to 400 g) were used in the following groups:
  crotamiton-sensitized group, acetamiton-sensitized group, butamiton-sensitized group, DNCB-sensitized group and non-sensitized group (n=7 with respect to each of the groups)
<Administration>
  (1) Intradermal sensitization
  On the day before administration, the neck and back of each guinea pig were shorn to set up a section (ca. 2×4 cm). As shown in FIG. 1, points 1 to 3 were fixed in the section.
  An emulsion comprising Freund's complete adjuvant (FCA) and distilled water for injection at a ratio of 1:1 was intradermally administered at the right and left points 1; a 10% (w/v) solution of a test compound in propylene glycol or a 0.1% (w/v) solution of DNCB therein at the right and left points 2; and an emulsion comprising a 20% (w/v) solution of a test compound in FCA or a 0.2% (w/v) solution of DNCB in FCA and distilled water for injection at a ratio of 1:1 at the right and left points 3, each in an amount of 0.05 ml per point.
  (2) Percutaneous sensitization
  One week after the beginning of sensitization, 0.2 g of a white soft paraffin ointment containing 10% of sodium laurate was applied to the intradermally sensitized section; and the next day, the ointment was removed with alcohol. Thus, pretreatment was conducted. Then, 0.2 ml of a solution of a test compound (40%, w/v) in ethanol (70%, v/v) or a solution of DNCB (1%, w/v) therein was applied to a filter paper (2×4 cm) and the resulting filter paper was stuck to the sensitized section occlusively for 48 hours. The non-sensitized group of guinea pigs were not subjected to any treatment.
  (3) Provocation
  Three weeks after the beginning of sensitization, an adhesive plaster for patch test coated with 0.2 ml of a solution of a test compound (30%, w/v) in ethanol (70%, v/v) or with 0.2 g of a white soft paraffin ointment containing 0.1% (w/v) of DNCB was stuck to the right side of abdomen of each guinea pig, while one coated with a 70% (v/v) ethanol solution or with a white soft paraffin ointment was stuck to the left side thereof in the same amount as above. Thus, the 24-hour closed test was conducted. In a similar manner as above, adhesive plasters for patch test coated with 0.2 ml of a solution of a test compound (30%, w/v) in ethanol (70%, v/v) and with 0.2 ml of 70% (v/v) ethanol respectively were stuck respectively to the right and left sides of abdomen of non-sensitized group of guinea pigs to conduct 24-hour closed test.

(4) Evaluation 24 and 48 hours after the peeling of the plaster, the guinea pigs were evaluated for dermoreaction according to the criteria specified in Table 7 (findings of skin and score).

TABLE 7

| Degree of skin response | Score |
| --- | --- |
| no change recognizable with the naked eye | 0 |
| slight or sparse erythema | 1 |
| medium erythema | 2 |
| significant erythema and edema | 3 |

Whether each test compound sensitizes the skin or not was judged by comparison with the DNCB-sensitized group and the non-sensitized group. The results are given in Table 8.

TABLE 8

| Sensitizer | Provocative | Number of guinea pigs | Time | Score 0 | 1 | 2 | 3 | Percentage of positive reaction | Average score |
| --- | --- | --- | --- | --- | --- | --- | --- | --- | --- |
| crotamiton | crotamiton | 7 | 24 | 7 | 0 | 0 | 0 | 0 | 0 |
|  |  |  | 48 | 3 | 4 | 0 | 0 | 57.1 | 0.57 |
|  | EtOH | 7 | 24 | 7 | 0 | 0 | 0 | 0 | 0 |
|  |  |  | 48 | 7 | 0 | 0 | 0 | 0 | 0 |
| acetamiton | acetamiton | 7 | 24 | 7 | 0 | 0 | 0 | 0 | 0 |
|  |  |  | 48 | 7 | 0 | 0 | 0 | 0 | 0 |
|  | EtOH | 7 | 24 | 7 | 0 | 0 | 0 | 0 | 0 |
|  |  |  | 48 | 7 | 0 | 0 | 0 | 0 | 0 |
| butamiton | butamiton | 7 | 24 | 6 | 1 | 0 | 0 | 14.3 | 0.14 |
|  |  |  | 48 | 6 | 1 | 0 | 0 | 14.3 | 0.14 |
|  | EtOH | 7 | 24 | 7 | 0 | 0 | 0 | 0 | 0 |
|  |  |  | 48 | 7 | 0 | 0 | 0 | 0 | 0 |
| DNCB | DNCB | 7 | 24 | 0 | 0 | 1 | 6 | 100 | 2.86 |
|  |  |  | 48 | 0 | 0 | 1 | 6 | 100 | 2.86 |
|  | white soft paraffin | 7 | 24 | 7 | 0 | 0 | 0 | 0 | 0 |
|  |  |  | 48 | 7 | 0 | 0 | 0 | 0 | 0 |
| No treatment | crotamiton | 7 | 24 | 7 | 0 | 0 | 0 | 0 | 0 |
|  |  |  | 48 | 7 | 0 | 0 | 0 | 0 | 0 |
|  | acetamiton | 7 | 24 | 7 | 0 | 0 | 0 | 0 | 0 |
|  |  |  | 48 | 7 | 0 | 0 | 0 | 0 | 0 |
|  | butamiton | 7 | 24 | 7 | 0 | 0 | 0 | 0 | 0 |
|  |  |  | 48 | 7 | 0 | 0 | 0 | 0 | 0 |
|  | EtOH | 7 | 24 | 7 | 0 | 0 | 0 | 0 | 0 |
|  |  |  | 48 | 7 | 0 | 0 | 0 | 0 | 0 |

It can be understood from the above results that acetamiton and butamiton do not sensitize the skin or the sensitization with them if any, is lighter and much weaker than that with crotamiton.

Test Example 5

Drug-release test

The tape-aids made in Examples 20 and 23 and Comparative Examples 1 and 2 were examined for release of drug into water. This experiment was made on both the samples just after production and the samples which had been allowed to stand at 60° C. for one month to thereby determine the stabilities of the preparations with the lapse of time. The preparations used are those containing estradiol (0.8 mg/10 cm$^2$). The results are given in FIG. 2 (just after production) and FIG. 3 (after allowed to stand at 60° C. for one month).

Figure 2:
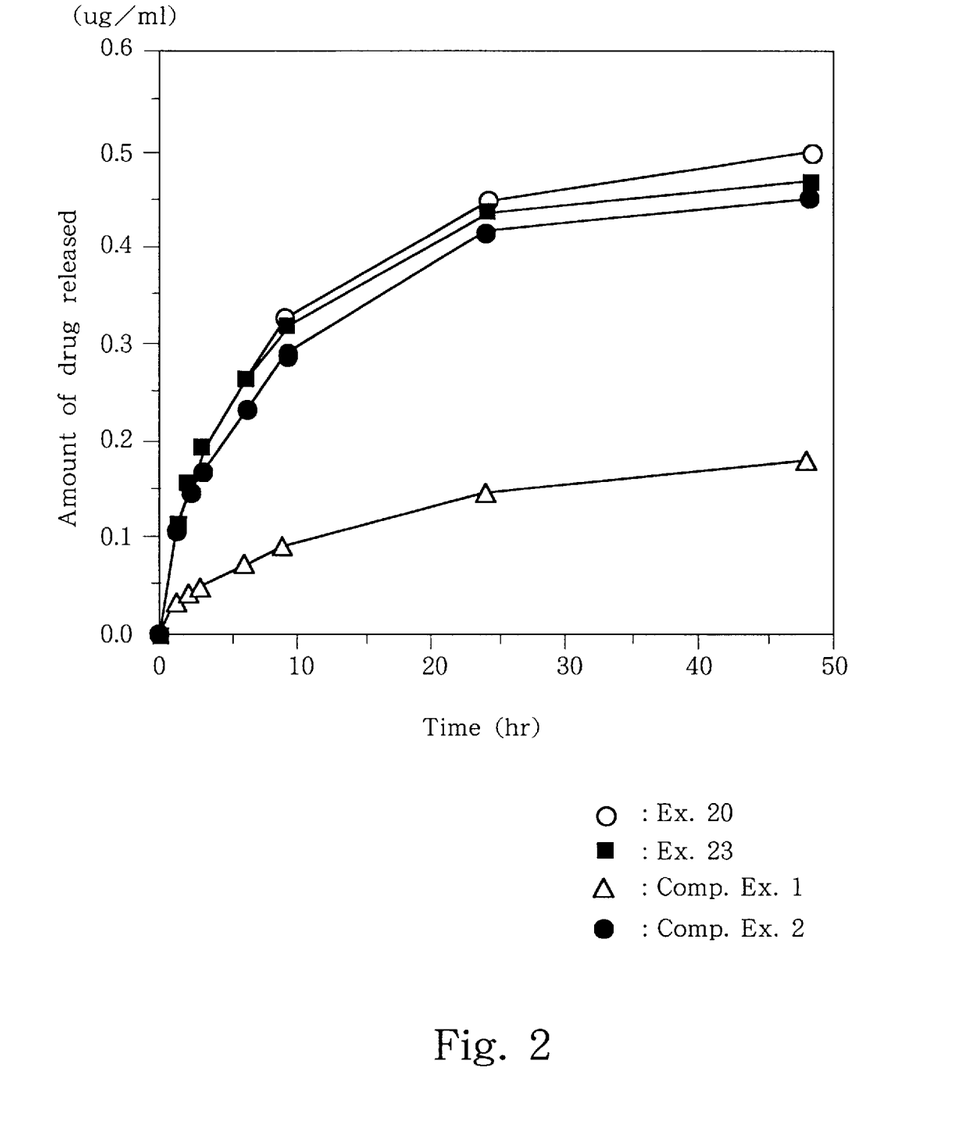
FIG. 2: Graphs showing the initial release of drugs from preparations
Figure 3:
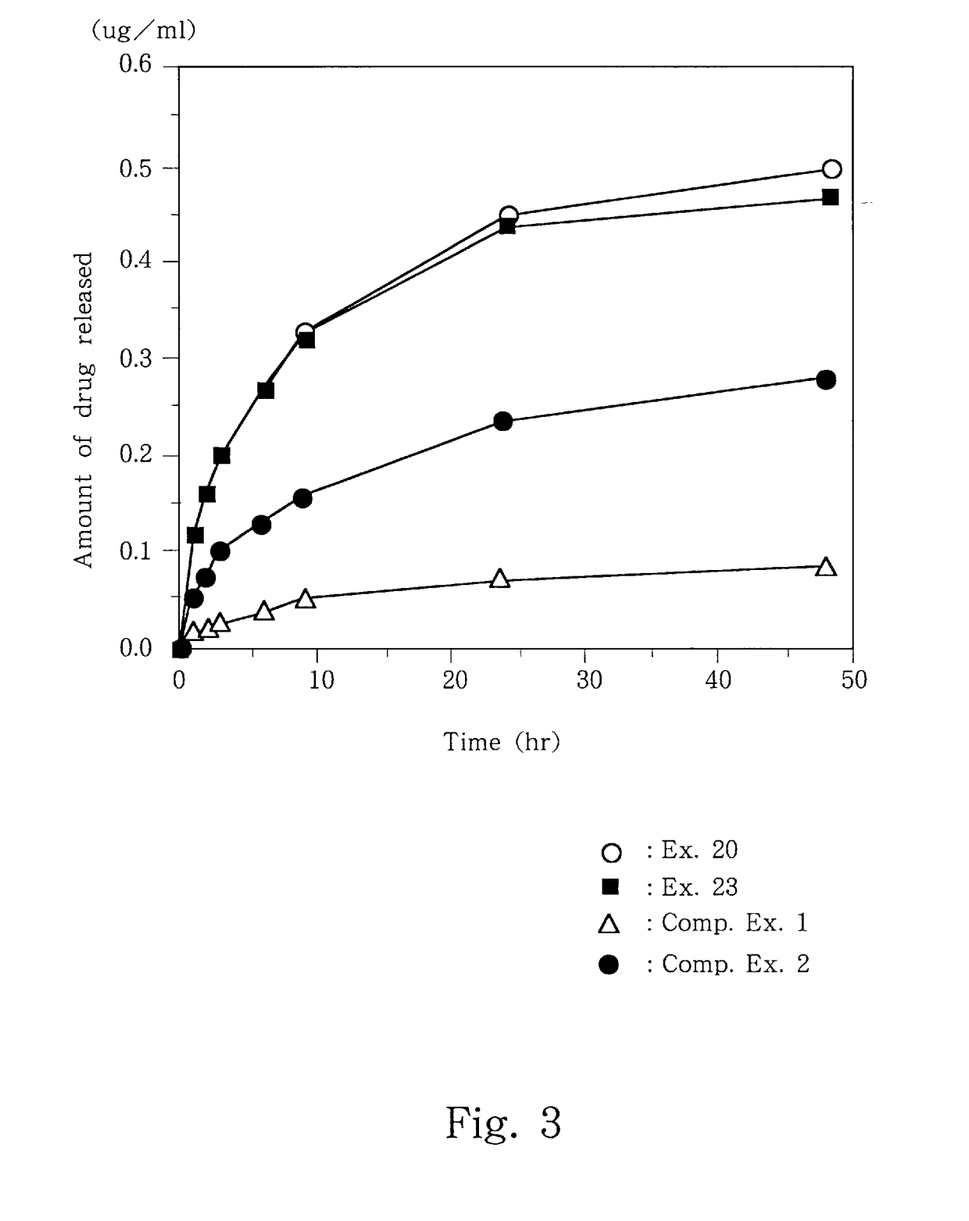
FIG. 3: Graphs showing the release of drugs from preparations after being allowed to stand at 60° C. for one month after the production

It can be understood from FIGS. 2 and 3 that the preparations made in Examples 20 and 23 exhibit more excellent drug-releasing properties than those of the preparations made in Comparative Examples 1 and 2 even after they have been allowed to stand at 60° C. for one month.

Test Example 6

Penetration test using hairless mouse skin (Experimental method)

The penetration of drugs was determined by the diffusion cell method using a piece of skin from the back of a female hairless mouse (aged 7 weeks).

Indomethacin (IM) and pindolol (PID) were used as the drugs (temperature of measurement: 22° C.). 0.5 ml of a solution containing a drug was added to the donor phase and the amount of the drug penetrating into the receptor phase was determined by high-performance liquid chromatography (HPLC). The solvents of the donor phase and the receptor phase were 50% ethanol/phosphate buffer (EtOH/PB, pH7.4) and 10% ethanol/phosphate buffer (EtOH/PB, pH7.4), respectively.

Among the N-substituted-o-toluidines,

N-acetyl-N-ethyl-o-toluidine (ACT)

N-propanoyl-N-ethyl-o-toluidine (PRT) and

N-butanoyl-N-ethyl-o-toluidine (BUT)

were used as drug-absorption accelerators and examined for drug-absorption accelerating effect in an aqueous system. In this examination, crotamiton (Cro.) and dimethyl sulfoxide (DMSO) were used as comparative compounds. The compositions of the donor phases are given in Tables 9 and 10.

TABLE 9

In the case of indomethacin

| Sample No. | IM | EtOH | PB | ACT | PRT | BUT | Cro. | DMSO |
|---|---|---|---|---|---|---|---|---|
| Control | 0.5 | 49.75 | 49.75 | | | | | |
| Test Ex. 1-A | 0.5 | 48.5 | 48.5 | 2.5 | | | | |
| Test Ex. 1-B | 0.5 | 48.5 | 48.5 | | 2.5 | | | |
| Test Ex. 1-C | 0.5 | 48.5 | 48.5 | | | 2.5 | | |
| Test Ex. 1-D | 0.5 | 48.5 | 48.5 | | | | 2.5 | |
| Test Ex. 1-E | 0.5 | 48.5 | 48.5 | | | | | 2.5 |

TABLE 10

In the case of pindolol

| Sample No. | PID | EtOH | PB | ACT | PRT | BUT | Cro. | DMSO |
|---|---|---|---|---|---|---|---|---|
| Control | 0.1 | 49.75 | 49.75 | | | | | |
| Test Ex. 1-F | 0.1 | 47.45 | 47.45 | 5.0 | | | | |
| Test Ex. 1-G | 0.1 | 47.45 | 47.45 | | 5.0 | | | |
| Test Ex. 1-H | 0.1 | 47.45 | 47.45 | | | 5.0 | | |
| Test Ex. 1-I | 0.1 | 47.45 | 47.45 | | | | 5.0 | |
| Test Ex. 1-J | 0.1 | 47.45 | 47.45 | | | | | 5.0 |

Figure 4:
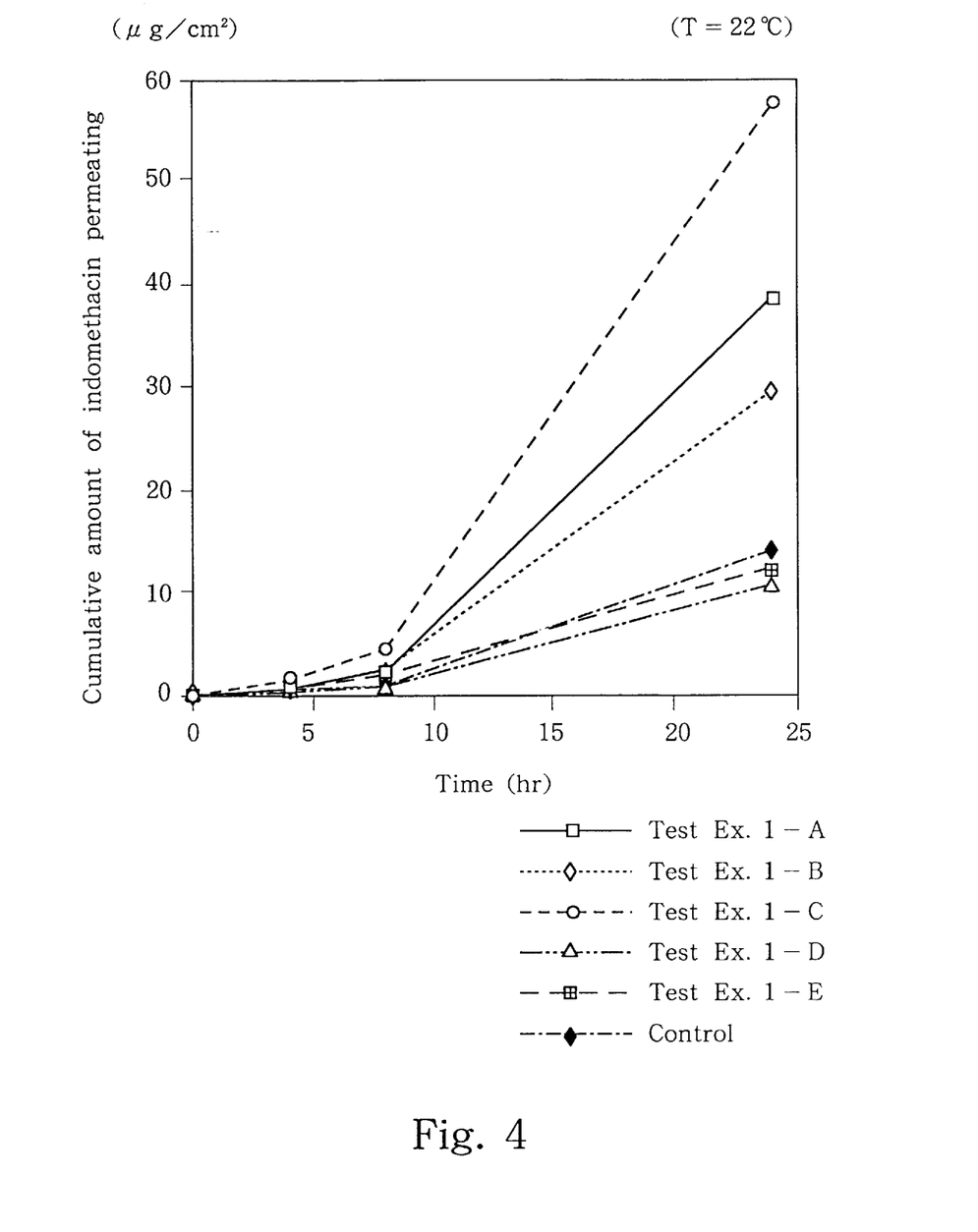
FIG. 4: Graphs showing the penetrability of indomethacin through the skin of hairless mouse
Figure 5:
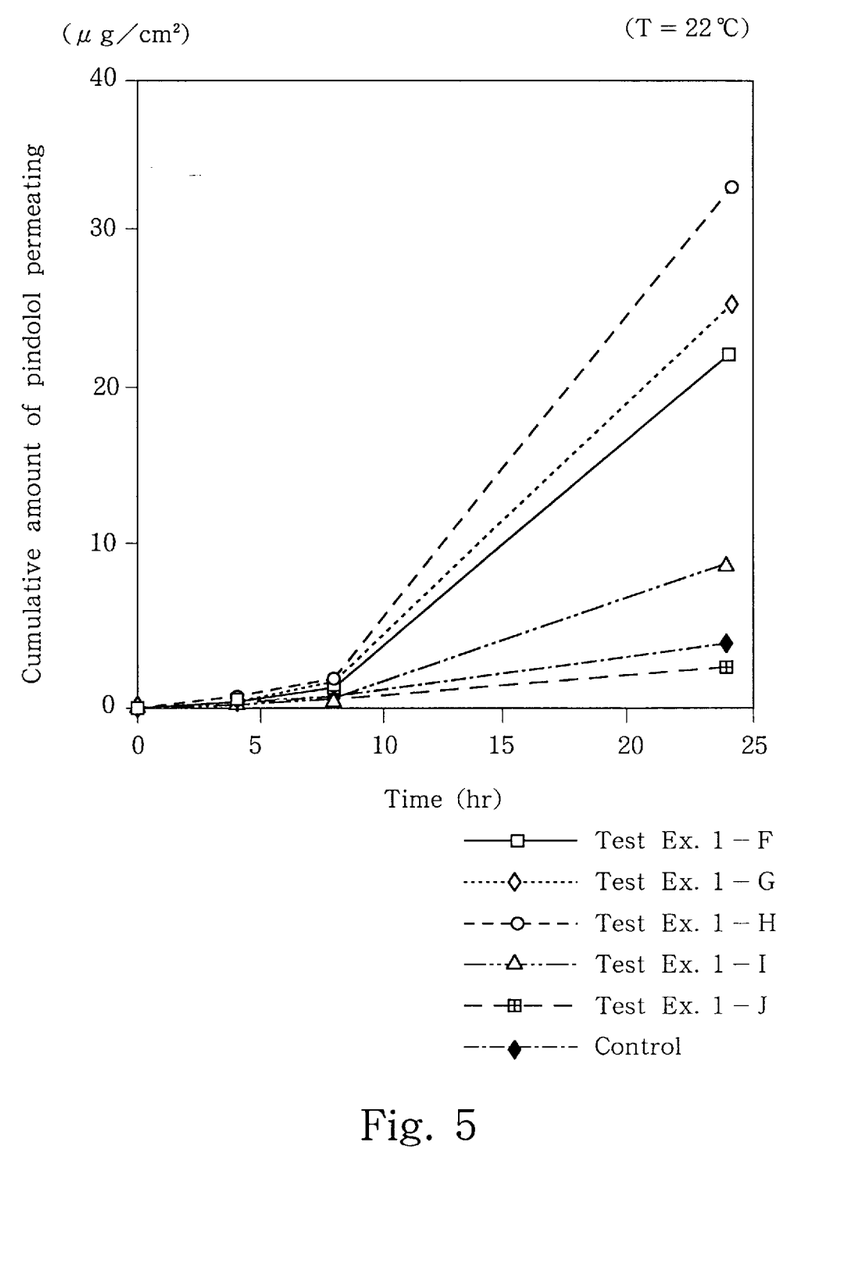
FIG. 5: Graphs showing the penetrability of pindrol through the skin of hairless mouse

The results are given in FIGS. 4 and 5. It can be understood from the results that the N-substituted-o-toluidine derivatives of this invention exhibit remarkable drug-absorption accelerating effect, when added to drugs.

Test Example 7

Percutaneous absorbability test using rabbit skin (Experimental method)

Japanese white rabbits (male, weight: ca. 2.5 to 3.0 kg) were used in groups of six. The rabbits were shorn by the use of an electric hair clipper and an electric razor, and the testosterone-containing tape-aids (7 cm$^2$, plaster weight: 80 mg) made in Examples 25 to 27 and Comparative Examples 4 to 6 were stuck to the back skins of the resulting rabbits occlusively. After the lapse of predetermined times, the tape-aids were peeled and examined for the amounts of drug remaining in the preparations by HPLC.

Method for determining the amount: Each peeled sample was extracted with 70 ml of ethanol under reflux for 3 hours; ethanol was added to the extract to make up to a total volume of 100 ml; and the resulting solution was used as the sample for HPLC.

Conditions of HPLC:

| | |
|---|---|
| mobile phase | 0.55:0.45 mixture of 0.2% acetic acid/water with acetonitrile |
| absorption wavelength | 241 nm |
| column | TSK gel ODS-80TM |
| flow rate | 1.0 ml/min |
| Absorbability (%): | 100 - (amt. of remaining drug/initial amt.) × 100 (each percutaneous absorbability was calculated by the above equation) |

The results are given in Table 11.

TABLE 11

| Test preparation | Rate of absorption through the back skin of rabbit (%) | |
|---|---|---|
| | 8 hours after | 24 hours after |
| Ex. 25 | 24.55 ± 9.64 | 42.54 ± 11.56 |
| Ex. 26 | 23.21 ± 9.23 | 35.96 ± 10.21 |
| Ex. 27 | 21.36 ± 11.83 | 31.08 ± 13.67 |
| Comp. Ex. 6 | 12.32 ± 7.66 | 19.54 ± 11.63 |
| Comp. Ex. 5 | 5.35 ± 4.84 | 12.94 ± 9.57 |
| Comp. Ex. 4 | 1.56 ± 1.17 | 3.36 ± 2.16 |

As apparent from the results given in Table 11, the compounds of this invention exhibit remarkable increases in the percutaneous absorbability of testosterone as compared with the control, and are superior to the comparative compounds in drug-absorption accelerating effect. In this experiment, no abnormality such as erythema or edema was observed in the areas to which the tape-aids containing the compounds of this invention were applied.

Test Example 8

Test for irritancy to the skin

The tape-aids made in Examples 25 to 27 and Comparative Examples 4 and 6 were examined for irritancy to the human skin.

The testing method is as follows.

Subjects: forty healthy male adults (age: 26 to 35)

Testing method: Each tape-aid was examined according to 48-hour closed patch test by punching circular pieces having a diameter of 15 mm out of each tape-aid, sticking the pieces to the upper backs of the subjects and covering the pieces with microporous tapes (mfd. by Minnesota Minning and Manufacturing Co.). After 48 hours, the tape-aids were peeled off. After the lapse of one and 24 hours from the peeling, the state of the skin was observed to evaluate the irritancy of each tape-aid to the skin. The results are given in Table 13 (the criteria and the equation for calculating skin irritation value are given in Table 12).

TABLE 12

Skin irritation evaluating criteria

| Degree of skin response | Evaluation | Score |
|---|---|---|
| no change | − | 0.0 |
| slight rubefaction | ± | 0.5 |
| obvious rubefaction | + | 1.0 |
| papule, edema | ++ | 2.0 |

$$\text{Skin irritation value} = \frac{\text{sum of higher one of two scores obtained for individual subjects 1 hour after peeling off and 24 hours after peeling off}}{\text{number of subjects}} \times 100$$

TABLE 13

| Sample | Lapse of time after peeling off | ++ | + | ± | − | Total | Percentage of positive reaction (%) ++ and + | ± | Skin irritation value |
|---|---|---|---|---|---|---|---|---|---|
| Ex. 25 | 1 hour | 0 | 0 | 5 | 35 | 40 | 0.0 | 12.5 | 6.3 |
|  | 24 hours | 0 | 0 | 2 | 38 | 40 | 0.0 | 5.0 |  |
| Ex. 26 | 1 hour | 0 | 0 | 3 | 37 | 40 | 0.0 | 7.5 | 5.0 |
|  | 24 hours | 0 | 0 | 1 | 39 | 40 | 0.0 | 2.5 |  |
| Ex. 27 | 1 hour | 0 | 0 | 3 | 37 | 40 | 0.0 | 7.5 | 3.8 |
|  | 24 hours | 0 | 0 | 1 | 39 | 40 | 0.0 | 2.5 |  |
| Comp. Ex. 4 | 1 hour | 0 | 1 | 7 | 32 | 40 | 2.5 | 20.0 | 11.3 |
|  | 24 hours | 0 | 0 | 2 | 38 | 40 | 0.0 | 5.0 |  |
| Comp. Ex. 6 | 1 hour | 0 | 0 | 5 | 35 | 40 | 0.0 | 12.5 | 7.5 |
|  | 24 hours | 0 | 0 | 4 | 36 | 40 | 0.0 | 10.0 |  |

As apparent from the results given in Table 13, the preparations containing drug-absorption accelerators of this invention exhibit lower skin irritation values than that of the preparation not containing any drug-absorption accelerator. Further, they exhibit skin irritation equivalent to that of the preparation containing crotamiton which has been conventionally used because it is known for its low skin irritation. Therefore, the drug-absorption accelerators of this invention are suitably usable for external preparations.

Industrial Applicability

As described above, the drug solubilizers of this invention each consisting of at least one of the N-substituted-o-toluidine derivatives are excellent in solvency for drugs and exhibit high safety, stability and compatibility with a base. Accordingly, the percutaneously absorbable preparations containing the solubilizers are improved in drug-releasing properties and percutaneous absorbability, so that the solubilizers are useful for pharmaceutical preparations for external use.

On the other hand, the drug-absorption accelerators of this invention each comprising at least one of the N-substituted-o-toluidine derivatives remarkably enhance the permeation or transmission of drugs through the skin, when added to the drugs in proper amounts. Further, they are lowly irritant to the skin and cause little skin sensitization, thus being extremely safe. Furthermore, they are excellent in compatibility with a base and have little adverse effect on the compatibility of a drug with a base, so that the preparations containing them are protected from precipitation of a drug in the crystal form.

The percutaneously absorbable preparations each comprising a drug and an N-substituted-o-toluidine derivative of this invention are very useful as topical preparations which are expected to exhibit pharmacological effects locally in skin, nose, cavity of mouth, rectum, vagina and so on, or as general drugs which are expected to exhibit systemic pharmacological effects.

What is claimed is:

1. A solubilizer for use with a drug and consisting of at least one compound selected from N-substituted-o-toluidines represented by the following formula (I):

wherein $R_1$ is a lower alkyl group having 1 to 4 carbon atoms and $R_2$ is an alkyl group having 1 to 8 carbon atoms.

2. A percutaneously absorbable preparation comprising the solubilizer of claim 1 and a drug.

3. A percutaneously absorbable preparation according to claim 2, wherein the solubilizer is present in an amount by weight of 0.01 to 20% of the total weight of the preparation.

4. An absorption accelerator for use with a drug and consisting of at least one compound selected from N-substituted-o-toluidines represented by the following formula (I):

wherein $R_1$ is a lower alkyl group having 1 to 4 carbon atoms and $R_2$ is an alkyl group having 1 to 8 carbon atoms.

5. A percutaneously absorbable preparation comprising the accelerator of claim 4 and a drug.

6. A percutaneously absorbable preparation according to claim 5, wherein the accelerator is present in an amount by weight of 0.1 to 20% of the total weight of the preparation.

7. A percutaneously absorbable preparation according to claim 2, which has a dosage form selected from the group consisting of poultice, ointment, gel, cream, gel-like cream, lotion, spray, tape-aid, reserver patch, liniment and aerosol.

8. A percutaneously absorbable preparation according to claim 3, which has a dosage form selected from the group consisting of poultice, ointment, gel, cream, gel-like cream, lotion, spray, tape-aid, reserver patch, liniment and aerosol.

9. A percutaneously absorbable preparation according to claim 5, which has a dosage form selected from the group consisting of poultice, ointment, gel, cream, gel-like cream, lotion, spray, tape-aid, reserver patch, liniment and aerosol.

10. A percutaneously absorbable preparation according to claim 6, which has a dosage form selected from the group consisting of poultice, ointment, gel, cream, gel-like cream, lotion, spray, tape-aid, reserver patch, liniment and aerosol.

* * * * *